United States Patent [19]

Viscontini et al.

[11] Patent Number: 4,650,864

[45] Date of Patent: Mar. 17, 1987

[54] PROCESS FOR PREPARING 5-DEOXY-L-ARABINOSE

[75] Inventors: Max Viscontini, Zürich, Switzerland; Subir Datta, Calcutta, India

[73] Assignee: Kanegafuchi Kagaku Kogyo Kabushiki, Osaka, Japan

[21] Appl. No.: 746,801

[22] Filed: Jun. 20, 1985

[30] Foreign Application Priority Data

Jun. 21, 1984 [JP] Japan .................................. 59-128208

[51] Int. Cl.$^4$ .............................................. C07H 1/00
[52] U.S. Cl. .................................. 536/124; 536/18.5; 536/4.1
[58] Field of Search ................. 536/1.1, 4.1, 124, 18.5

[56] References Cited

U.S. PATENT DOCUMENTS 4,384,998  5/1983  Durette ................................ 536/4.1

OTHER PUBLICATIONS

Carey et al, *Advanced Organic Chemistry*, Part B, pp. 474–475, 1977.
Pigman, *The Carbohydrates*, 1957, p. 165.
Mitra et al, Helv. Chmi. Acta 38, 1, (1955).
Weygand et al, Chem. Ber. 103, 2437–2499, (1970).
Karrer, Lehrbuch Der Organischen Chemie, 182, 364, (1959).

*Primary Examiner*—Johnnie R. Brown
*Assistant Examiner*—Elli Peselel
*Attorney, Agent, or Firm*—Armstrong, Nikaido, Marmelstein & Kubovcik

[57] ABSTRACT

The process for preparing 5-deoxy-arabinose comprises reacting 5-tosyl-L-arabinose-dialkylmercaptal with NaBH$_4$ in DMSO to give 5-deoxy-L-arabinose-dialkylmercaptal and then reacting the obtained 5-deoxy-L-arabinose-dialkylmercaptal with hydrochloric acid in DMSO. According to the process, 5-deoxy-L-arabinose can be obtained in a high yield without employing heavy metal such as mercury.

2 Claims, No Drawings ture was sufficiently stirred by a stirrer. After the mixture was cooled down to 0° C., L-(+)-arabinose was added thereto in portions of about 3 to 4 g for 10 to 20 minutes with rapid and sufficient stirring. After addition of L-(+)-arabinose with total amount of 60 g (0.4 mole), stirring was continued for 1 hour, wherein the whole mixture became solid when addition was almost completed. The obtained solid was filtered, washed with 500 ml of water and dried over a Buchner funnel in air for about 2 hours. And then, the obtained solid was crystallized from 800 ml of boiling water. Water was put to boil, and when the water started to boil, the solid was added in small portions to the water with stirring in such a way that every portion was added immediately after the dissolution of the previously added portion. After all the solid was added to the water and the mixture became an almost clear solution (slightly emulsified), the clear solution was filtered in a sufficiently hot condition and the filtrate was cooled overnight. The cooled filtrate was further filtered and the obtained solid was dried in a desiccator of give 94.3 g of L-(+)-arabinose-diethyl mercaptal (yield: 92%).

REFERENCE EXAMPLE 2

[Preparation of 5-tosyl-L-(+)-arabinose-dimethylmercaptal]

A 500 ml two necked flask equipped with a thermometer and a pressure balancing funnel was charged with 14.08 g (55 mmoles) of L-(+)-arabinose-diethylmercaptal obtained in Reference Example 1. Thereto 84 ml of pyridine was added and the mixture was stirred until a clear solution was obtained. Then, the solution was sufficiently cooled to −5° C. on an ice-Nacl bath.

A solution of 11.5 g (60 mmoles) of tosylchloride in 40 ml of pyridine was slowly added to the above cooled solution was stirring for about 2 hours wherein the temperature of the former solution was maintained below 0° C. After addition of the tosylchloride solution, the reaction mixture was slowly heated to room temperature for 2 to 3 hours. Then, the ice-Nacl bath was removed and the flask was allowed to stand at room temperature overnight. Next morning, the reaction mixture in the flask was poured slowly into 1200 ml of ice-water with stirring and the mixture was allowed to stand for 10 minutes. The solid was filtered and washed with 30 ml of cold water 4 times. The thus obtained solid was dissolved in 200 ml of ethylacetate and the solution was washed successively with a cold dilute hydrochloric acid, dilute sodium hydrogencarbonate solution and water until the solution became neutral. After the solution was dried with sodium sulfate, the solvent was removed off. There was dissolved 19.1 g of the obtained solid residue into 75 ml of chloroform and precipitated with 300 ml of pentane. The precipitate was filtered and dried in air to give 18.4 g of the desired product (yield after crystallization: 82%).

EXAMPLE

A 1000 ml round flask was charged with 4 g (105 mmoles) of NaBH$_4$, and thereto 100 ml of DMSO was added. The mixture was stirred by magnetic stirrer until the mixture became an almost clear solution. To the solution there was slowly added 100 ml of DMSO containing 20 g (49 mmoles) of 5-tosyl-L-(+)-arabinose-diethylmercaptal for about 2 hours with stirring. After addition, the mixture was further stirred for half an hour at room temperature. Then, the mixture was heated on a water bath for one hour at 90° C with occasional stirring. After the mixture was evaporated to dryness on a water bath of 90° C. under vacuum (1 Torr), the mixture was cooled and the obtained residue was decomposed with ice water. A small amount of scum was filtered off and the obtained clear filtrate (pH>13) was made slightly acidic with 5% acetic acid. After the filtrate was thoroughly extracted with ether, the ether layer was dried with sodium sulfate and the solvent was evaporated from the ether layer to give 9.5 g of 5-deoxy-L-(+)-arabinose-diethylmercaptal as a white solid residue (yield: 81%).

The residue had a melting point of 109° C. and a specific rotatory power $[\alpha]_D^{18}$ of +27° (C=1.30, in methanol) and the result agreed with that reported by B. Green et al. in "Chem. Berichte", 99, 2162 (1966).

There was reacted 9.5 g (40 mmoles) of 5-deoxy-L-(+)-arabinose-diethylmercaptal obtained in the above reaction with 11 g (140 mmoles) of DMSO in 100 ml of 6N hydrochloric acid at room temperature and the mixture was mechanically stirred for about 4 hours until all solid was dissolved into a solution.

After further stirring for 1 hour, a mixture comprising two homogeneous liquids was obtained. The mixture was transferred to a separatory funnel and allowed to precipitate. The lower aqueous layer was separated, cooled on an ice-NaCl bath and adjusted to pH 6.5 with 6N sodium hydroxide. The solvent was evaporated under condition close to vacuum as far as possible and the precipitated sodium chloride was filtered off through a glass filter crucible. The precipitate was thoroughly washed with 10 ml of ethanol 5 times. The collected filtrate was evaporated and once more sodium chloride was filtered. The procedures of the above filtration, washing with alcohol (provided that methanol which dissolves 5-deoxy-L-arabinose more sufficiently was employed on and after the second washing) and evaporation, which were repeated 5 times so that the separation of sodium chloride was unnecessary, gave 5.0 g of 5-deoxy-L-arabinose as a syrup (yield: 93%).

The obtained product had specific rotatory power $[\alpha]_D^{25}$ of +25.3° (C=0.3, in methanol) and the result agreed with that reported by J. Kiss et al. in "Helvetica Chimica Acta", 58, 311 (1975).

REFERENCE EXAMPLE 3

There was added 5.0 g (37.3 mmoles) of 5-deoxy-L-(+)-arabinose obtained in Example to 80 ml of methanol and the mixture was stirred to give a clear solution. With stirring there was added dropwise 4.5 g (42 mmoles) of phenylhydrazine to the obtained mixture and thereto further a drop of glacial acetic acid was added. Thus obtained yellow solution was allowed to stand for 1 hour at room temperature and then the solution was evaporated under a condition close to vacuum as far as possible to give a thick viscous residue. After the residue was washed with 30 ml of ether twice, the residue was dissolved in 150 ml of ethyl acetate. The thus obtained solution was washed with about 40 ml of water twice, the organic layer was dried with sodium sulfate and the solvent was evaporated under vacuum. There remained a pale yellow skin-like solid on the bottom of the flask. The solid was washed with 30 ml of ether twice (for half an hour per each washing) and dried to give 8.0 g of 5-deoxy-L-arabinose-phenylhydrazone (yield: 96%).

PROCESS FOR PREPARING 5-DEOXY-L-ARABINOSE

BACKGROUND OF THE INVENTION

The present invention relates to a process for preparing 5-deoxy-L-arabinose. 5-Deoxy-L-arabinose is useful as a starting material for preparing 5,6,7,8-tetrahydro-L-biopterin being useful for treatment of patients with Parkinson's disease or depression as well as phenylketone urea.

A process employing L-rhamnose as a starting material and another process employing L-arabinose as a starting material have been known for preparing 5-deoxy-L-arabinose. However, it is not preferable to employ L-rhamnose in large amount in industry since L-rhamnose is costly.

As a process employing L-arabinose which is easily obtained in industry as a starting material, there has been known a process where tosylated L-arabinose-diethylmercaptal is reduced with lithium aluminum hydride (hereinafter referred to as "LiAlH$_4$") to give 5-deoxy-L-arabinose-diethylmercaptal and then the obtained 5-deoxy-L-arabinose-diethylmercaptal is converted to 5-deoxy-methyl-L-arabinofuranoside by defulfurization and O-methylation, and further the obtained 5-deoxy-methyl-L-arabinofuranoside is reacted with hydrochloric acid to give 5-deoxy-L-arabinose as reported by B. Green and H. Rembold in "Chem. Berichte", 99, 2162 (1966). However, the above process is not preferable for industrially preparing 5-deoxy-L-arabinose because LiAlH$_4$ which is costly and dangerous must be employed as a reductant and mercuric chloride (hereinafter referred to as "HgCl$_2$") which has associated problems in industrial usage must be employed in desulfurization.

And also, a process by which 5-deoxy-D-arabinose is obtained from 5-tosyl-D-arabinose-diethylmercaptal via 5-deoxy-D-arabinose-diethylmercaptal has been disclosed by H. Zinner et al. in "Chem. Berichte", 92, 1618 to 1623 (1959). However, this process also employed LiAlH$_4$ and HgCl$_2$ as in the case of the process disclosed by Green et al. That is, deoxygenation reaction in this process is carried out in the presence of LiAlH$_4$ in a mixed solvent of benzene and ethyl ether. However, the desired compound in this reaction is obtained only in less than 60% yield. Successive desulfurization is carried out in acetone containing water in the presence of mercury oxide and HgCl$_2$ and the recovery of mercury is carried out by passing hydrogen sulfide through the resultant. However, the yield is less than 50% and moreover it is very difficult to recover mercury completely. Therefore, this process is not industrially suitable.

In the process for preparing 5-deoxy-L-arabinose, the present inventors have found that sodium boron hydride (hereinafter referred to as "NaBH$_4$") which is cheap and quite safe can be employed as a reductant and desulfurization of 5-deoxy-L-arabinose-dialkylmercaptal can be carried out in the reaction system of dimethylsulfoxide (hereinafter referred to as "DMSO")-hydrochloric acid to give a high yield without employing mercury, and the like.

An object of the present invention is to provide a process for preparing 5-deoxy-L-arabinose from 5-tosyl-L-arabinose-dialkylmercaptal in a high yield without employing a heavy metal such as mercury.

SUMMARY OF THE INVENTION

According to the present invention, 5-deoxy-L-arabinose is prepared by reacting 5-tosyl-L-arabinose-dialkylmercaptal with NaBH$_4$ in DMSO to give 5-deoxy-L-arabinose-dialkylmercaptal and then reacting the obtained 5-deoxy-L-arabinose-dialkylmercaptal with hydrochloric acid in DMSO.

DETAILED DESCRIPTION

The process of the present invention comprises two step reactions as follows:

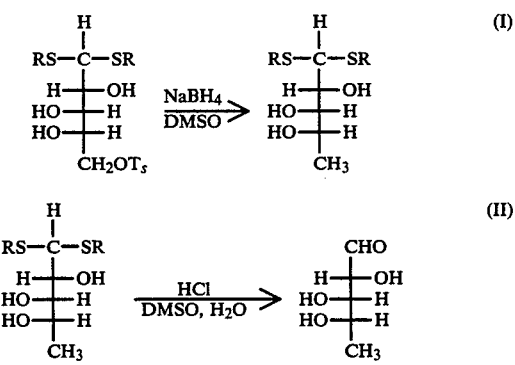

wherein R is an alkyl group having 1 to 4 carbon atoms, preferably ethyl group.

The reaction (I) is carried out for 1 to 5 hours at 0° to 150° C., preferably 20° to 100° C. On the other hand, the reaction (II) is carried out for 1 to 5 hours with stirring at 5° to 50° C., preferably 15° to 30° C.

According to the present invention, the yield of the reaction (I) is not less than 80% and the yield of the reaction (II) is not less than 90%. Therefore, the desired products can be obtained in a high yield in both of the two reactions. And also, DMSO employed as a solvent can be easily recovered by distillation. Therefore, it is possible to decrease the cost for preparing.

There can be prepared 5-tosyl-L-arabinose-dialkylmercaptal which is a starting material of the present invention, for instance, by reacting tosylchloride with L-arabinose-dialkylmercaptal which is obtained by reacting alkylmercaptan with L-arabinose.

There can be obtained 5-deoxy-L-arabinose-phenylhydrazone which is a starting material of 5,6,7,8-tetrahydro-L-biopterin by reacting phenylhydrazine with 5-deoxy-L-arabinose which is a desired compound of the present invention, and 5,6,7,8-tetrahydro-L-biopterin can be prepared from 5-deoxy-L-arabinose by means of a known method described by Max Viscontini et al. in "Helvetica Chimica Acta", 60, 211 (1977), the same, 61, 2731 (1978), and the like.

The present invention is more particularly described and explained by the following Examples. However, it is to be understood that the present invention is not limited to the Examples, and various changes and modifications may be made in the invention without departing from the spirit and scope thereof.

REFERENCE EXAMPLE 1

[Preparation of L-(+)-arabinose-diethylmercaptal]

A 400 ml beaker cooled on an ice-NaCl bath was charged with 104 ml (1.4 moles) of ethylmercaptan and 72 ml of concentrated hydrochloric acid and the mix- The obtained product had the following analytical values.

Elementary analysis: $C_{11}H_{16}O_3N_2$ (for molecular weight of 224.27): Calcd.(%): C 58.91 H 7.19 N 12.49. Found (%): C 59.37 H 7.67 N 11.16.

$^1$H-NMR analysis (δ value, ppm) (CD$_3$OD): 7.35 to 6.55 (m, 5H), 7.19 (d, 1H), 4.45 (q, 1H), 3.87 (m, 1H), 3.48 (q, 1H) and 1.28 (d, 3H).

What we claim is:

1. A process for preparing 5-deoxy-L-arabinose which comprises reacting 5-tosyl-L-arabinose-dialkylmercaptal having the formula:

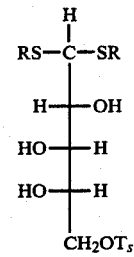

wherein R is an alkyl group having 1 to 4 carbon atoms, with NaBH$_4$ in dimethylsulfoxide to give 5-deoxy-L-arabinose-dialkylmercaptal having the formula:

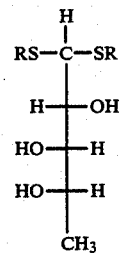

wherein R is an alkyl group having 1 to 4 carbon atoms, and then reacting the obtained 5-deoxy-L-arabinose-dialkylmercaptal with hydrochloric acid in dimethylsulfoxide.

2. The process of claim 1, wherein R in said 5-tosyl-L-arabinose-dialkylmercaptal is ethyl.

* * * * *

UNITED STATES PATENT AND TRADEMARK OFFICE
CERTIFICATE OF CORRECTION

PATENT NO. : 4,650,864
DATED : March 17, 1987
INVENTOR(S) : MAX VISCONTINI ET AL It is certified that error appears in the above-identified patent and that said Letters Patent is hereby corrected as shown below:

On the cover page, Item [73], after "Kabushiki" insert --- Kaisha ---.

Signed and Sealed this

Tenth Day of November, 1987

*Attest:*

DONALD J. QUIGG

*Attesting Officer*  *Commissioner of Patents and Trademarks*